(12) United States Patent
Malowaniec

(10) Patent No.: US 8,905,990 B2
(45) Date of Patent: Dec. 9, 2014

(54) INCONTINENCE ARTICLE IN PANTS FORM

(75) Inventor: Krzysztof D. Malowaniec, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 568 days.

(21) Appl. No.: 13/138,832

(22) PCT Filed: Apr. 7, 2010

(86) PCT No.: PCT/EP2010/002166
§ 371 (c)(1),
(2), (4) Date: Oct. 6, 2011

(87) PCT Pub. No.: WO2010/127750
PCT Pub. Date: Nov. 11, 2010

(65) Prior Publication Data
US 2012/0046632 A1 Feb. 23, 2012

(30) Foreign Application Priority Data
Apr. 17, 2009 (EP) .................................... 09005461

(51) Int. Cl.
*A61F 13/496* (2006.01)
*A61F 13/49* (2006.01)

(52) U.S. Cl.
CPC ..... *A61F 13/49011* (2013.01); *A61F 13/49061* (2013.01); *A61F 13/496* (2013.01)
USPC .............. 604/385.31; 604/385.01; 604/385.21

(58) Field of Classification Search
CPC ............ A61F 13/49061; A61F 13/539; A61F 2013/53908; A61F 2013/53925; A61F 2013/5395; A61F 2013/53991
USPC ........................... 604/385.01, 385.21, 385.31
See application file for complete search history.

(56) References Cited

U.S. PATENT DOCUMENTS

| 6,217,563 | B1 | 4/2001 | Van Gompel et al. | |
| 2005/0148965 | A1* | 7/2005 | Richlen et al. | 604/367 |
| 2008/0114325 | A1* | 5/2008 | Edwall et al. | 604/385.24 |

FOREIGN PATENT DOCUMENTS

| EP | 1 473 008 | 11/2004 |
| JP | 2008194161 | 8/2008 |
| WO | 02/091974 | 11/2002 |

*Primary Examiner* — Tan-Uyen (Jackie) T Ho
*Assistant Examiner* — Peter S Vasat
(74) *Attorney, Agent, or Firm* — Paul Vincent

(57) ABSTRACT

The invention relates to an incontinence article (2) in the form of underpants, wherein the crotch segment (8) overlaps the belly segment (4) in a front overlapping area (36) and the crotch segment (8) overlaps with the back segment (6) in a rear overlapping area (38), wherein the outside (86) of the crotch segment (8) is inseparably joined to the inside (41) of the belly segment (4) in a front connecting area (306) and the outside (86) of the crotch segment (8) is inseparably joined to the inside (41) of the back segment (6) in a rear connecting area (308), wherein the connecting area (306, 308) of the belly segment (4) and the rear segment (6) each comprise a first joining area (310), 312) and second joining areas (314a, 314b, 316a, 316b), wherein the first joining area (310, 312) extends at least in segment below the absorption body (7), and wherein the second joining areas (314a, 314b, 316a, 316b) are provided in an area (320a, 320b, 322a, 322b) crossing each longitudinal edge (48) of the crotch segment (8), thus flashing both a partial area (324a, 324b, 326a, 326b) of the overhang (66a, 66b) of the crotch segment (8) and a partial area (328a, 328b, 330a, 330b) of the belly segment (4) and/or the back segment (6) adjacent thereto, and wherein each second joining area (314a, 314b, 316a, 316b) extends in the longitudinal direction (9), starting from a transverse edge (58, 60) of the belly segment (4) and/or the back segment (6) facing the crotch, in the direction toward the longitudinal ends (98, 100) of the crotch segment (8), and wherein each second joining area (314a, 314b, 316a, 316b) is formed by joining means (340) in the form of welding points, particularly ultrasonic welding points, thermal welding points, and/or calender welding points, so that the second joining areas (314a, 314b, 316a, 316b) form reinforcement areas (334a, 334b, 336a, 336b).

24 Claims, 7 Drawing Sheets

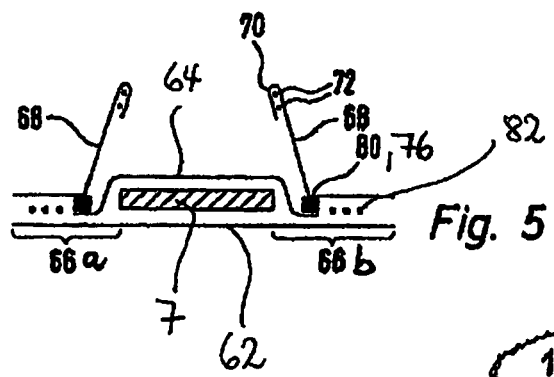
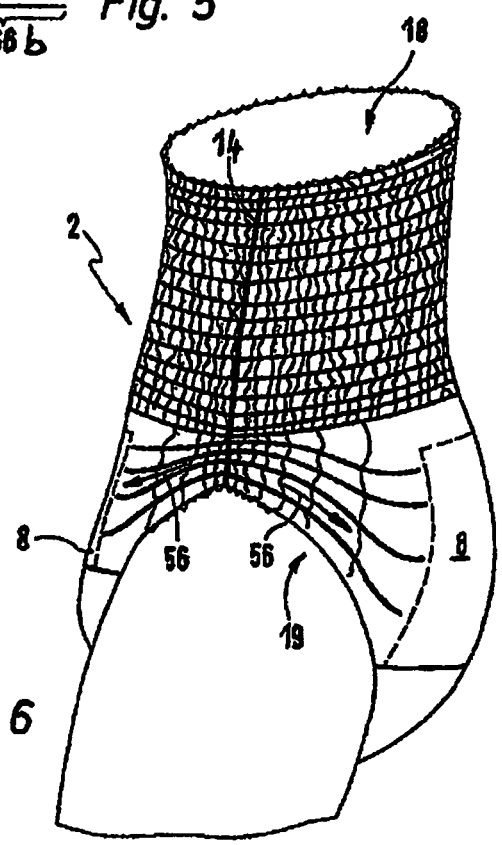
Fig. 5
Fig. 6

INCONTINENCE ARTICLE IN PANTS FORM

This application is the national stage of PCT/EP2010/002166 filed on Apr. 7, 2010 and claims Paris Convention Priority of EP 09 005 461, filed Apr. 17, 2009.

BACKGROUND OF THE INVENTION

The invention relates to an incontinence article in pants form for receiving body excretions, with a front stomach portion and a rear back portion, which to form a stomach and back band which is continuous in the transverse or waist-encircling direction and has a waist opening that is closed in the waist-encircling direction are connected to one another at the manufacturer's at side seam regions on both sides, and with a crotch portion, which has an absorbent body, extends in a longitudinal direction between the stomach portion and the back portion and is inseparably joined to the stomach portion and to the back portion in connecting regions, wherein not only the crotch portion but also the stomach portion and the back portion bound the leg openings of the incontinence article. An incontinence article produced in this way from three components is known, for example, from WO 2004/052260 A1, WO 03/039423 A1, WO 2005/067842 A1, WO 2005/016200 A1 and EP 1 392 212 B1. In the case of this specific product concept, after the joining of the crotch portion, made to extend in the longitudinal direction, to the stomach portion, made to extend substantially in the transverse or waist-encircling direction, and the back portion, made to extend correspondingly, in the spread-out flat state, these three components can create an H-shaped basic structure of the incontinence article. The incontinence article is then formed in a modular manner from the components crotch portion, stomach portion and back portion. These components are advantageously first connected to one another by way of the crotch portion, and, preferably, after that the stomach portion is connected to the back portion in side seam regions on both sides. This is a connection performed at the manufacturer's, by which the pants form is obtained. This connection is typically inseparable. The pants form may, however, also be separable, in particular along a predetermined breaking line, which may in particular run in the side seam region, for example for removing a used incontinence article from a person needing care.

Incontinence articles in pants form are different in principle from traditional openable and closable incontinence articles in the customary diaper form in that the waist size is generally predetermined and the adaptation to different body sizes is achieved on the basis of a number of standard sizes by an elastic stretchability of the article. Generally used for this purpose are elasticating means, in particular in the form of bands or threads, often referred to as Lycra threads, connected in the pre-stretched state (stretch-bonding process) to chassis materials of the incontinence article, that is to say they are fixed in the pre-stretched state to the chassis materials, for example by means of an adhesive. As a result of their pretensioning, these elasticating means gather the chassis materials together and thereby form pleatings. The incontinence article or the elasticated chassis materials of the incontinence article can then stretch again elastically when the incontinence article is put onto the user like a pair of pants. Incontinence articles in pants form with such elasticated chassis materials are known in many instances and, for example, are also discussed in the previously mentioned WO 2004/052260 A1.

With the present invention it has been realized that, during the operation of putting on the incontinence article in pants form, in particular when engaging the lateral regions of the chassis materials, there is a crumpling, sometimes in certain regions creasing, of the chassis materials provided with elasticating means, accompanied by a twisting of the chassis materials. This represents an impairment of the elasticating effect and consequently of the fit; the visual impression is also disadvantageously impaired.

Against this background, the present invention is based on the object of counteracting the problems described above, without involving any impairment of the wearing comfort or further consequences impairing the functionality of the incontinence article.

SUMMARY OF THE INVENTION

This object is achieved according to the invention by an incontinence article with the features of the independent claim.

Advantageous developments of the incontinence article are provided by the respective subclaims.

The arrangement of the joining means within a first and/or second joining region may in this case be over the full surface area.

The arrangement of the joining means within a first and/or second joining region may also not be provided over the full surface area. Joining means which are not arranged over the full surface area within a joining region may preferably be provided in the form of a puntiform, strip-form or linear arrangement or some other pattern-like arrangement within the joining region. In the case of joining means not arranged over the full surface area, the joining region also comprises the unjoined regions present between the joining means. The association of joining means not arranged over the full surface area with a joining region is preferably determined by a repetitive arrangement of preferably identical joining means with the joining means spaced apart from one another by at most 10 mm. In the case of joining means not arranged over the full surface area, the areal extent of the joining region in the longitudinal and transverse directions is bounded with the aid of an imaginary connecting line through the respectively outer, that is to say distally situated, and neighboring joining means or the outermost peripheral edges thereof.

The reinforcing region formed by the second joining region has the dimensions determined for the second joining region in the longitudinal direction and transverse direction.

"Beneath the absorbent body" is understood here as the positioning of an areal extent that is extended over by the absorbent body in the transverse and longitudinal directions in plan view of an incontinence article laid out flat. Moreover, "joining region beneath the absorbent body" describes the arrangement of the joining region in the Z direction, to be specific between the absorbent body and the inner side of the stomach portion or back portion.

"Inner side" of the crotch portion, stomach portion or back portion is understood here as meaning respectively the upper side of the component to be considered that is facing the body of the user. Correspondingly, "outer side" is understood as meaning respectively the upper side of the component to be considered that is facing away from the body of the user, and consequently facing the clothing.

The figures given for lengths and/or widths of the incontinence article as such or of defined regions, such as for example the joining regions and subregions thereof, are always based on dimensions on the incontinence article in its laid-out flat and spread-out flat state.

"Overhang" is understood here as meaning the extent of the topsheet material or the topsheet material and the backsheet material in the transverse direction laterally outside the longitudinal peripheries of the absorbent body, the maximum extent being used in each case, that is to say the outer extent of the topsheet material and/or the backsheet material situated distally furthest from the longitudinal peripheries of the absorbent body. The backsheet material and/or the topsheet material may advantageously consist of a number of components, thus for example the topsheet material may advantageously be a composite of a topsheet material and barrier means adjacent on both sides in the longitudinal direction. It is therefore understood that, even in the case of composites, that is to say composed topsheet materials and/or backsheet materials in which the individual plies do not cover one another congruently, when considering the overhang, the maximum outer extent of the composite, or of the individual material plies occurring therein, that is to say the outer extent situated distally furthest away, is used in each case. The overhang is respectively assigned the width H.

"Side region of the stomach portion and/or back portion" is understood here as meaning the extent of the chassis material of the stomach portion and/or back portion laterally outside the respective longitudinal periphery of the crotch portion in the transverse direction to the respective longitudinal peripheral portion of the stomach portion or back portion. In this case, as explained above, the maximum extent, that is to say the outer extent that is situated distally furthest away, of the topsheet material and/or of the backsheet material is used as the longitudinal periphery of the crotch portion. The side region of the stomach portion and/or of the back portion is respectively assigned the maximum possible width N. Also in the case where the crotch-side portion of the stomach portion or of the back portion that is facing the leg openings has a peripheral contour deviating from the transverse or waist-encircling direction and running in the direction of a transverse center axis of the crotch portion, thus in particular if this peripheral contour is arcuately shaped, the maximum width N is always used. In other words, the width N is always the distance measured in the transverse direction from the longitudinal periphery of the crotch portion to the longitudinal periphery of the stomach portion or back portion, which then forms the side seam regions of the incontinence article.

With the invention it has been recognized that such a construction of an incontinence article in pants form is accompanied by major advantages:

The formation of a second joining region in the form of welding locations has the effect of forming reinforcing regions, which allow a stiffening of the overhang of the crotch portion that is only in certain regions and is variable in extent. This has the advantage that the first and/or second elasticating means are arranged, at least in a subregion, between two stiffened panels extending in a longitudinal direction, which run substantially transversely, at least with a significant component in the transverse direction, to the first and/or second elasticating means. While one reinforcing region forms a first stiffened panel, the side seam usually represents a second stiffened panel. This has a positive evening-out effect on the distribution of the restoring forces of the first and/or second elasticating means gathering the chassis materials in this subregion. As a consequence, very uniform gathering can take place there and the undesired pleatings of the chassis materials, and accompanying uncontrolled twisting of the chassis materials, can be counteracted. This consequently has a positive effect on the fit of the incontinence article.

The fact that the connecting regions of the crotch portion to the stomach portion and to the back portion correspondingly comprise in each case first and second joining regions also makes it possible for the connection between the crotch portion and the stomach portion or back portion to be configured and designed appropriately for the requirements of the respective regions of the incontinence article:

It has been recognized that the absorbent body is stabilized in its positioning within the incontinence article, in particular with respect to the flexible chassis materials of the stomach and back portions, by the first joining region, which runs at least in certain portions beneath the absorbent body. This is advantageous since, during the process of putting on an incontinence article in pants form, which differs considerably from the process of putting on a traditional diaper of the open type, forces act on the entire incontinence article. While the diaper of the open type is correspondingly put flat onto the body of the user, without any great tensile forces acting, and is then subsequently closed, when putting on the pants-type diaper that is closed at the manufacturer's, for example when pulling it up between the legs, the absorbent body and the plies neighboring it are exposed to deforming forces that are anything but inconsiderable. A disadvantageous deformation, and possibly permanent significant displacement, of the crotch portion in relation to the chassis materials of the stomach and back portions is prevented by the attachment at least in certain portions beneath the absorbent body.

It is advantageous that the second joining region in this case extends over both a subregion of the overhang respectively, and then passes over the longitudinal periphery of the crotch part into the subregion adjacent thereto of the stomach portion and of the back portion. The fact that the second joining region is provided in a region bridging the longitudinal periphery of the crotch portion means that the direct longitudinal periphery of the crotch portion is securely attached to the chassis materials of the respective stomach or back portion. This is advantageous since uncontrolled protrusion of the overhang of the crotch portion, and consequently uncontrolled folding that may lead to hard locations, are prevented.

Furthermore, the forming of a second joining region with joining means in the form of welding locations, in particular ultrasonic welding locations, thermal welding locations and/or calender welding locations, has a further advantage:

The use of adhesive materials also gives rise to the problem when the incontinence articles are produced by machine that extremely precise positioning of the adhesive material is required, but not readily achievable in high-speed diaper machines, in order to prevent the adhesive materials from escaping over the peripheral region, and consequently prevent the sticking together of regions and materials not intended for this within the incontinence article or between a number of incontinence articles. The escape of adhesives also leads to contamination of the tools of the machine during the production of the incontinence article. The use of joining means in the form of welding locations has the effect of avoiding the unwanted escape of adhesive material caused by the production equipment. Moreover, the joining means in the form of welding locations ultimately provide a reinforcing region without introducing further additional material components, which saves costs.

The features of the independent claim altogether provide an incontinence article in pants form with the three-component structure mentioned, in which a secure connection of the components can be realized and the described disadvantages of the prior art are overcome, to be precise without involving any impairment of the wearing comfort or the functionality of the incontinence article or its components, but instead significantly improving the fit of the incontinence article.

In a development of the invention, it proves to be advantageous if the second joining regions, and consequently the reinforcing regions, extend, when considered in the longitudinal direction, from the crotch-facing transverse periphery of the stomach portion and of the back portion continuously to at least the respective longitudinal end of the crotch portion.

The second joining regions, provided in the longitudinal direction in the front and/or rear connecting region along the longitudinal periphery of the crotch portion, are preferably in each case arranged symmetrically to one another and preferably also have in each case the same design, so that they therefore coincide, for example, with regard to longitudinal extent, width, degree of overlap, type of joining means and/or arrangement of the joining means and/or combinations thereof.

Depending on the application area of the incontinence article and also the mobility of the user, it may be advantageous to design the second joining regions differently in the front and rear connecting regions. Preferably, the second joining regions in the front and rear connecting regions differ at least in one of the parameters longitudinal extent, width, degree of overlap, type of joining means and/or arrangement of the joining means and/or combinations thereof.

Depending on the area of use of the incontinence article and also the mobility of the user, it may be advantageous to design the second joining regions differently in the longitudinal extent in the front and rear connecting regions. More preferably, the second joining regions have a greater longitudinal extent in the rear connecting region than in the front connecting region.

In an advantageous way, a respective second joining region is arranged outside the contour of the absorbent body, that is to say outside the longitudinal peripheries thereof.

In an advantageous way, the second joining region has in the extended-over subregion of the overhang in the transverse direction a width P' of greater than 1 mm, preferably greater than 2 mm, more preferably greater than 5 mm, but preferably of less than 60 mm, preferably less than 50 mm, more preferably less than 40 mm, more preferably less than 30 mm, more preferably less than 20 mm.

In a further advantageous way, the proportion P'/H of the subregion of the respective overhang that is extended over by the second joining region, with the width P' with respect to the respective overhang with a width H in the front and/or rear overlapping region, is at least 0.01, particularly at least 0.04, more particularly at least 0.07, more particularly at least 0.10, but preferably at most 0.90, particularly at most 0.80, more particularly at most 0.70, more particularly at most 0.60, more particularly at most 0.50, more particularly at most 0.40.

This proportion of the joining region in the respective overhang allows adequate reinforcement of the attachment of the chassis-forming shell materials to the crotch portion to be achieved, without the flexibility of the overhang being impaired to any considerable extent.

In an advantageous way, the respective overhang has a width H preferably of at least 10 mm, more particularly of at least 20 mm, more particularly of 20 to 100 mm, more particularly of 20 to 80 mm.

More advantageously, the second joining region extends over the subregion of the stomach portion and/or back portion that is adjacent the longitudinal periphery of the crotch portion in the transverse direction respectively with a width P''' of greater than 1 mm, preferably greater than 2 mm, more preferably greater than 5 mm, but preferably of less than 60 mm, preferably less than 50 mm, more preferably less than 40 mm, more preferably less than 30 mm, more preferably less than 20 mm.

Particularly advantageously, the proportion P'''/H of the respective subregion of the stomach portion and/or back portion that is extended over by the second joining region, with the width P''' with respect to the respective overhang with a width H, is at least 0.01, particularly at least 0.04, more particularly at least 0.07, more particularly at least 0.10, but preferably at most 0.90, more particularly at most 0.80, more particularly at most 0.70, more particularly at most 0.60, more particularly at most 0.50, more particularly at most 0.40.

Advantageously, the second joining region, and consequently the reinforcing region, has an overall width P of 5-60 mm, particularly of 10-50 mm, more particularly of 10-40 mm, more particularly of 10-30 mm.

Particularly advantageously, the proportion P'''/N of the respective subregion of the stomach portion and/or back portion that is extended over by the second joining region, with the width P''' with respect to the respective side region of the stomach portion and/or back portion with a width N, is at least 0.01, particularly at least 0.015, more particularly at least 0.020, but preferably at most 0.35, particularly at most 0.30, more particularly at most 0.25, more particularly at most 0.20, more particularly at most 0.15, more particularly at most 0.10.

This proportion of the second joining region, and consequently the reinforcing region, in the respective side region of the stomach portion and/or back portion allows adequate reinforcement to be achieved, without these chassis materials and their elasticating means fixed therein being impaired in their flexibility and also the way in which they act over a large surface area.

In an advantageous way, the proportion P'/N of the respective subregion of the respective overhang that is extended over by the second joining region, with the width P' with respect to the respective side region of the stomach portion and/or of the back portion with a width N, is at least 0.01, particularly at least 0.015, more particularly at least 0.020, but preferably at most 0.35, particularly at most 0.30, more particularly at most 0.25, more particularly at most 0.20, more particularly at most 0.15, more particularly at most 0.10.

In an advantageous way, a the respective side region of the stomach portion and/or of the back portion extends in the transverse direction with a width N of preferably at least 100 mm, more preferably of at least 120 mm, and particularly 120 mm to 350 mm, more particularly 120 to 320 mm.

In an advantageous way, the second joining region with the overall width P is arranged along the longitudinal periphery of the crotch portion in such a way that the ratio of the width P' to the width P''' is preferably between 1:4 and 4:1, more preferably between 1:3 and 3:1, more preferably between 1:2 and 2:1, particularly preferably 1:1.

In a further advantageous way, the second joining region is arranged parallel to the longitudinal direction with a constant overall width P. This allows the second joining region to be introduced into the incontinence article in a technically uncomplicated manner, and consequently also more quickly and at lower cost.

In a further advantageous way, the joining means in the second joining region have been introduced from the inner side of the crotch portion and the corresponding stomach portion and/or back portion in such a way that the attached surface areas obtained by the joining means, to be specific the welding locations, are oriented from the inner side in the direction of the outer side. However, the joining means have particularly been introduced in such a way that the welding locations are not pressed through to the outer side of the stomach portion and/or back portion, and consequently are not perceptible or scarcely perceptible.

In an advantageous development, the joining means in the second joining region are provided over the full surface area. In this way, the second joining region can be introduced into the incontinence article in a technically uncomplicated manner, and consequently also at low cost.

In the case of this preferred embodiment, the surface area attached by the joining means has a proportion of 100% of the overall surface area encompassed by the second joining region.

In a further advantageous development, the joining means in the second joining region are not provided over the full surface area. Particularly, the joining means within the second joining region are provided in the form of a pattern, particularly in the form of a puntiform and/or strip-form and/or linear arrangement and/or some other pattern-like arrangement and/or in combinations thereof. As a result, the extent of the stiffening of the second joining regions can be advantageously set. As described above, the stiffening has an advantageous effect on the fit; however, excessive stiffening may lead to uncomfortable hard locations.

In a further advantageous way, the sum of the joining means not arranged over the full surface area in the second joining region assumes an attached surface area (joining locations) with a proportion of at least 1.5%, particularly at least 2.0%, more particularly at least 2.5% and preferably of almost 60%, more particularly and most 50%, more particularly at most 40%, more particularly at most 30%, more particularly at most 20%, with respect to the overall surface area extended over by the second joining region.

In a particularly advantageous way, the joining means in the second joining region are arranged in a point pattern and the sum of the surface area attached by the joining means (joining locations) assumes a proportion of at least 1.5%, particularly at least 2.0%, more particularly at least 2.3%, more particularly at least 2.5%, and preferably at most 20.0%, particularly at most 15%, more particularly at most 10.0%, more particularly at most 8.0%, more particularly at most 7.0%, more particularly at most 6.0%, with respect to the overall surface area extended over by the second joining region.

In a further advantageous way, the surface areas attached by the single joining means in a point pattern in the second joining region have a diameter of at least 0.2 mm, particularly of at least 0.3 mm, more particularly of at least 0.4 mm, more particularly of at least 0.5 mm and preferably of at most 2.5 mm, particularly of at most 2.0 mm, more particularly of at most 1.5 mm, more particularly of at most 1.2 mm, more particularly of at most 1.0 mm.

In particular, the neighboring individual joining means present in a point pattern are respectively arranged spaced apart from one another by 1-10 mm, particularly by 1-8 mm, more particularly by 1-6 mm, more particularly by 1-5 mm, more particularly by 1.5-4.5 mm, more particularly by 2-4 mm; particularly preferably at the same distance.

For a first joining region, non-adhesive joining means may advantageously be used, particularly taken from the group of welding locations, more particularly ultrasonic welding locations, thermal welding locations and/or calender welding locations. It has moreover proven to be particularly advantageous to use as joining means in a first joining region an adhesive, particularly a hotmelt adhesive. More particularly, the adhesive or hotmelt adhesive has hydrophobic properties. This is advantageous since, in addition to the connecting function, a liquid barrier is formed at the same time.

In the first joining region, the crotch portion may advantageously be connected to the stomach portion and/or to the back portion by means of an application of adhesive that is not over the full surface area. An application of adhesive that is not over the full surface area may be, for example, a strip-form pattern, a web-form continuous or discontinuous grid structure or insular regions or else a strip-form or spirally arranged adhesive structure.

It has moreover proven to be particularly advantageous to use in the first joining region an application of adhesive over the full surface area. This provides optimized attachment of the crotch portion, with an absorbent body that is in itself torsionally stiff, to the rather more flexible chassis materials of the stomach portion and/or back portion and prevent undesired displacement of the components in relation to one another.

Advantageously, the first joining region extends beneath the absorbent body at least up to the longitudinal peripheries of the absorbent body, but ends before the longitudinal peripheries of the crotch portion. More advantageously, the first joining region extends in the transverse direction over the longitudinal peripheries of the absorbent body in such a way that an overlap with the respective second joining region is obtained.

The chassis-forming materials of the stomach portion and/or back portion preferably comprise nonwoven materials, such as spunbonded nonwovens (S), meltblown nonwovens (M), SM nonwovens, SMS nonwovens, SMMS nonwovens, carded nonwovens or through-air bonded carded nonwovens. Particularly preferably, the chassis-forming material of the stomach portion and/or back portion comprises spunbonded nonwoven. The nonwoven materials used for the stomach portion and/or back portion advantageously have a basis weight of 10-30 g/m$^2$, more preferably of 15-25 g/m$^2$. Particularly preferably, the stomach portion and the back portion comprise a spunbonded nonwoven of polypropylene, particularly with a basis weight of 15-25 g/m$^2$.

For the forming of the crotch portion, a backsheet material or a topsheet material with low basis weights, to be specific of 10-40 g/m$^2$ and 5-20 g/m$^2$, respectively, is preferably used. This advantageously realizes the softness, adaptability and drape that are desired for the user of the incontinence article in these sensitive regions of the body.

The chassis-forming shell materials of the crotch portion are further advantageously formed:
the backsheet particularly comprises a sheeting, particularly of a basis weight of 10-40 g/m$^2$. In particular, the backsheet comprises a sheeting which is liquid-impermeable during use, but at the same time breathable, that is to say water-vapor-permeable, particularly microporous. The water-vapor permeability of the backsheet is particularly at least 300 g/m$^2$/24 h, more particularly at least 1000 g/m$^2$/24 h, more particularly at least 2000 g/m$^2$/24 h, more particularly at least 3000 g/m$^2$/24 h, more particularly at least 4000 g/m$^2$/24 h, more particularly at most 6000 g/m$^2$/24 h, measured in accordance with DIN 53 122-1 (edition: 2001-08).

The sheeting may advantageously also be provided with a nonwoven coating, which can impart a textile look to the outer side of the incontinence article that is facing away from the body. The nonwoven coating preferably consists of a nonwoven material, particularly a spunbonded nonwoven of polypropylene, particularly with a basis weight of 7-25 g/m$^2$, 10-20 g/m$^2$, particularly of 12-17 g/m$^2$.

The topsheet material preferably comprises nonwoven materials, such as spunbonded nonwovens (S), meltblown nonwovens (M), SM nonwovens, SMS nonwovens, SMMS nonwovens, carded nonwovens or through-air bonded carded nonwovens.

The topsheet material may in this case preferably be formed only from topsheet material. More preferably, the topsheet material may be a composite of topsheet material and barrier means. In a further advantageous form, the topsheet material is a composite of a liquid-permeable topsheet material with longitudinal peripheries and adjacent longitudinal peripheral regions and hydrophobic barrier means joined onto the longitudinal peripheries or longitudinal peripheral regions on both sides of the topsheet material at bonding locations. This composite provides an incontinence article with the different requirement profiles region by region, to be specific a liquid absorption in the central region and a slowing of the lateral escape of liquid at the peripheral regions.

Corresponding to the functionality, advantageous materials given below are used:

The topsheet material preferably comprises nonwoven materials, such as spunbonded nonwovens, carded nonwovens or through-air bonded carded nonwovens. Particularly preferably, the topsheet material comprises spunbonded nonwoven. More advantageously, the nonwoven materials used for the topsheet have a basis weight of 5-20 $g/m^2$, 8-20 $g/m^2$, more preferably of 10-18 $g/m^2$, particularly preferably of 12-16 $g/m^2$. Particularly preferably, the topsheet comprises a hydrophilicized spunbonded nonwoven, particularly of polypropylene, particularly with a basis weight of 12-16 $g/m^2$.

The material of the barrier means preferably comprises nonwoven materials, such as spunbonded nonwovens, meltblown nonwovens, carded nonwovens or through-air bonded carded nonwovens. Particularly preferably, the material of the barrier means comprises single-ply or multi-ply nonwovens. Particularly preferably, the material of the barrier means comprises laminates of one or more plies of spunbonded nonwoven (S) and/or meltblown nonwoven (M), particularly SMS laminates or SMMS laminates, particularly based on polyolefins, such as for example polyethylene or polypropylene. Such materials are inexpensive and, on account of their inherently hydrophobic property, suitable for having a liquid-retardant effect.

More advantageously, the nonwoven materials used for the barrier means have a basis weight of 5-20 $g/m^2$, preferably of 8-20 $g/m^2$, more preferably of 10-18 $g/m^2$. Particularly preferably, the barrier means comprises a laminate of spunbonded nonwoven and meltblown nonwoven plies, particularly of polypropylene, particularly with a basis weight of 10-18 $g/m^2$.

In a further configuration, the hydrophobic barrier means extends over the longitudinal peripheries of the topsheet material, to be precise to form a barrier means respectively running in the longitudinal direction on both sides of the absorbent body that is in each case upright and is typically referred to as a cuff element or leg-band element. The distal ends of the barrier means are advantageously provided with elasticating means. In this way, the barrier means are raised against the surface of the user's skin during use of the incontinence article.

The fixing of the material webs of the topsheet-material composite at the joining locations may preferably take place by means of adhesive, particularly hotmelt adhesive, thermal calendering (thermobonding) or ultrasonic welding. The fixing may take the form of continuous joining locations, in order to achieve a high bonding force between the topsheet material and the barrier means. A continuous line is conceivable here. However, fixing by intermittently applied joining locations is also conceivable and advantageous, that is to say by a sequence of discrete points of attachment or lines of attachment or any other pattern of attachment.

The backsheet material and the topsheet material advantageously have the same extent in the transverse direction. They are congruent in relation to one another. It is also more advantageous, however, if the backsheet material and the topsheet material are not congruent in relation to one another. Particularly advantageously, the backsheet material has a narrower extent in the transverse direction in comparison with the topsheet material. In this way, the backsheet material, such as for example a sheeting, which possibly detracts from the wearing comfort for the user, is covered over by the skin-friendly nonwoven material of the topsheet material.

In a development of the invention, it proves to be advantageous if the proportion of the overall surface area of the incontinence article that is made up by the surface area of the crotch portion is 25-55%, particularly 30-47%, more particularly 35-47% and more particularly 35-45%.

In a development of the invention, the overlapping region between the crotch portion and the stomach portion is formed such that the crotch portion overlaps 15-40%, particularly 15-35% and more particularly 15-25% of the surface area of the stomach portion. In an advantageous way, the crotch portion overlaps the stomach portion with a surface area of 25,000-45,000 $mm^2$.

In a development of the invention, the overlapping region of the crotch portion and the back portion is formed such that the crotch portion overlaps 20-40%, particularly 20-35% and more particularly 22-32% of the surface area of the back portion. In an advantageous way, the crotch portion overlaps the back portion with a surface area of 35,000-65,000 $mm^2$, particularly of 40,000-55,000 $mm^2$.

The overlapping of the crotch portion with the back portion is advantageously greater than the overlapping of the crotch portion with the stomach portion.

In the case of the form of the incontinence article according to the invention, it is possible and advantageous if the absorbent body also overlaps 5-20%, particularly 5-15%, of the surface area of the stomach portion and/or 10-20%, particularly 10-15%, of the surface area of the back portion.

The extent of the stomach portion and of the back portion in the side seam region in the longitudinal direction is advantageously at least 100 mm, particularly at least 150 mm and particularly 150 mm to 250 mm.

The minimum distance between the stomach portion and the back portion in the longitudinal direction is advantageously 250 to 400 mm.

The maximum extent of the crotch portion in the transverse direction, that is to say the greatest width E, is advantageously at least 200 mm, particularly 200 to 350 mm, more particularly 250 to 320 mm.

Furthermore, it proves to be advantageous if the overhang of the backsheet material and/or of the topsheet material in the transverse direction is in total, that is to say on both sides of the longitudinal peripheries of the absorbent body, at least 25%, particularly 25-50%, more particularly 30-45% and more particularly 35-45%, with respect to the greatest width E of the crotch portion. The relatively large overhang of backsheet material and/or topsheet material on both sides of the absorbent body therefore means a wide crotch portion with a relatively narrow absorbent body. This makes it possible to provide in the crotch portion leg elasticating means that are made to extend along the leg openings and are at a relatively great distance from the bulky, and therefore rigid, absorbent body. This in turn results in good sealability and adaptability of the leg opening peripheries on both sides of the crotch portion. This is because the bulky absorbent body that is torsionally rigid in comparison with thin chassis materials is in this way of only little hindrance to the forming of a liquid-tight leg termination; it is therefore not necessary to work with extremely high tensions to form a liquid-tight leg termination, which in turn has a positive effect on the wearing comfort of the incontinence article.

In yet a further form of the invention, it proves to be particularly advantageous if the leg elasticating means end in the longitudinal direction at least 10 mm, particularly at least 20 mm, before the second elasticating means. It is particularly advantageous if the leg elasticating means end in the longitudinal direction before the stomach portion and/or before the back portion. The tension and restoring force exerted by them therefore does not influence the tension conditions of the second elasticating means. The tension conditions are particularly not influenced within the crotch-side region of the stomach portion and of the back portion that is facing the leg openings, in which the second elasticating means are provided in a fanning-out manner.

Preferably used as leg elasticating means are elasticating means in the form of threads or bands, such as rubber or polyether-polyurethane or polyester-polyurethane threads, preferably elastic threads such as Lycra®, Creora® or Spandex® threads. The leg elasticating means preferably have a thickness of 300-1500 dtex, particularly of 500-1200 dtex, more particularly 500-900 dtex. The leg elasticating means are preferably fixed with a pretensioning of 1.5-6.0, particularly of 2.5-4.5 on the chassis-forming shell materials of the crotch portion. The pretensioning is defined as a factor of the degree of stretching with respect to the unstretched/relaxed state of the elasticating means.

For the areal elastification of the stomach portion and back portion, the first elasticating means are provided, respectively spaced apart from one another and made to extend parallel to one another in the transverse or waist-encircling direction. These preferably have the same pretensioning and serve substantially for an areally continuous, uniform elastification of the stomach portion and of the back portion in the region well above the leg openings. It is however possible for the first elasticating means to have a stronger pretensioning in an upper peripheral region of the waist or for a number of these elasticating means to be provided in a closely spaced manner, in order to realize a somewhat stronger elastification at the periphery of the waist.

In yet a further form of the present invention, it has also been recognized that the tension conditions in said crotch-side region of the stomach portion and of the back portion that is facing the leg openings are essential with regard to the wearing comfort and can be made such that the wearing comfort is improved. Advantageously, the second elasticating means extend from the two side seam regions in the direction of a longitudinal center axis of the incontinence article and thereby run in an arcuately fanning-out manner with increasing distance from one another.

For this, the crotch-side region that is facing the leg openings, in which the second elasticating means fan out in the direction of the longitudinal center axis, is preferably formed such that, when this region is stretched over its surface area, the restoring force thereby occurring decreases in the direction of the crotch portion.

If this crotch-side region of the stomach portion and of the back portion that is facing the leg openings is thus considered, to be precise in a direction from the respective side seam region toward the crotch portion, that is to say in the direction of a longitudinal center axis of the incontinence article and to a certain extent in the direction of the arcuate fanning-out of the second elasticating means, the restoring force occurring in this direction when it is stretched out over its surface area is reduced. The force concerned here is therefore the force with which the stomach portion and the back portion resist stretching over the surface area. A decrease in this restoring force, which then of course is transferred to the user, is accomplished by a considerable improvement in the wearing comfort of the incontinence article.

It also proves to be particularly advantageous if the decrease in the restoring force in said crotch-side region of the stomach portion and of the back portion that is facing the leg openings is provided such that, in the direction of the crotch portion, a decreasing number of folds per centimeter are formed in the transverse direction of the incontinence article. In such a way, the stomach portion and the back portion can stretch in a way corresponding to the body shape of the user, without the elastic forces formed thereby causing the chassis material to gather with a multitude of folds. It should once again be explained at this point that the decrease in the restoring force in the direction of the crotch portion means that the force that is produced as a result of stretching over the surface area becomes less with increasing proximity to the crotch portion. The restoring force as a result of stretching over the surface area is therefore greater in an area nearer the side seam than in an area nearer the crotch portion.

Said tension conditions can be achieved in a variety of ways, for instance by using materials of different elasticity in the transverse direction in the crotch-side region that is facing the leg openings, in which the second elasticating means are also provided. It would also be conceivable for the pretensioning of the second elasticating means to be reduced with increasing proximity to the crotch portion, that is to say from the outside inward in the direction of a longitudinal center axis. It would also be conceivable for the decrease in the restoring force when stretching over the surface area to be achieved by increasing the distance between the second elasticating means, it having to be ensured here that this is not compensated by a strong increase in the pretensioning as a result of the fan-shaped line followed by the elasticating means, or even exceeded in the direction of increasing restoring force.

To determine the restoring forces, the regions of the chassis to be measured may be firmly clamped directly, as it were non-destructively, between two clamping jaws of a defined, identical clamping jaw width, and the restoring forces determined under defined stretching of the regions to be measured that simulates the state of use, by particularly 30% or 50% or 80% of the initial length (of the clamping jaw spacing when fixing the region to be measured in the unclamped state). The clamping jaws should fix as many elasticating means as possible, but at least two arranged next to one another, of the region to be measured and be oriented substantially perpendicularly with respect to the line followed by the elasticating means, so that the stretching takes place between the clamps substantially in the direction of the line followed by the elasticating means.

It has particularly proven to be advantageous if a minimum distance between the two elasticating means (spacing of elastification means lying directly next to one another) in the side seam regions is 3 to 8 mm, particularly 3 to 7 mm and more particularly 3 to 6 mm.

Furthermore, it has proven to be advantageous if a maximum distance between the two elasticating means (spacing of elastification means lying directly next to one another) at a periphery of the absorbent body or at a longitudinal periphery of the crotch portion is 7 to 35 mm, particularly 10 to 32 mm and more particularly 12 to 30 mm.

Furthermore, it has proven to be advantageous if the second elasticating means have a degree of fanning out F $$F=(A-B)/B*100\%$$

of 50 to 900%, particularly of 100 to 700% and more particularly of 150 to 550%.

The degree of fanning out F is defined as the ratio of the decrease in distance (A–B) to the minimum distance (B) in percent. The variables A and B are defined here as the distance of the outermost second elasticating means in the longitudinal direction from the innermost second elasticating means in the longitudinal direction (that is to say not the spacing of second elasticating means lying directly next to one another), to be precise A as the maximum distance, particularly at the longitudinal periphery of the crotch portion or at the periphery of the absorbent body, and B as the minimum distance particularly in the side seam region. It has also been recognized that it proves to be advantageous if the degree of fanning out F of the second elasticating means is greater in the back portion than in the stomach portion.

On account of the natural shapes of the body in the back region or stomach region of a user, the problems addressed here typically prove to be more serious in the back or buttocks region. To this extent, it proves to be advantageous if the maximum distance between the two elasticating means at a periphery of the absorbent body is greater in the back portion than in the stomach portion.

In an advantageous embodiment, the respective second joining regions, and consequently the reinforcing regions, extend, when considered in the longitudinal direction, from the crotch-facing transverse periphery of the stomach portion and of the back portion in the direction of the longitudinal ends of the crotch portion, to be precise at least up to the length consequently covered by the second elasticating means running arcuately from the side seam regions in the direction of the longitudinal center axis of the incontinence article, and particularly fanning out with increasing distance and finishing at the longitudinal periphery of the crotch portion. More advantageously, the respective second joining regions, and consequently the reinforcing regions, extend from the crotch-facing transverse periphery of the stomach portion and of the back portion, when considered in the longitudinal direction, at least up to the length that coincides with the placement of an imaginary horizontal line level with the height of the side seam region from which the arcuately running, and particularly fanning-out, second elasticating means begin. As described at the beginning, the stiffening by means of the reinforcing region provided by the second joining region has an advantageous effect on the fit.

It would be entirely conceivable for the second elasticating means to run continuously from one side seam region to the other side seam region, which particularly simplifies introduction in a continuous production process in comparison with a "cut-and-place" process. As a result of the coverage of the crotch portion with the stomach portion and with the back portion, there may, depending on the design, also be an overlapping or coverage of the bulky absorbent body with the stomach portion and/or the back portion, and consequently also with that crotch-side region of the stomach portion and of the back portion that is facing the leg openings in which the two elasticating means run. The bulky absorbent body in this case usually hinders elastic stretchability of the chassis materials. Furthermore, it is not necessarily advantageous if the bulky absorbent body is subjected to additional tensioning forces. It may therefore prove to be advantageous if the second elasticating means are deactivated with regard to their elastic properties in an overlapping region with the absorbent body of the crotch portion. This deactivation may be realized, for example, by a number of separating cuts through the second elasticating means in the region of the coverage with the absorbent body, while other separating methods, such as for example by means of ultrasonic welding or laser, are also conceivable.

It should be mentioned that the first elasticating means may also be deactivated with regard to their elastic properties in a region of coverage with the absorbent body.

With regard to the overall dimensions of the incontinence article, it proves to be advantageous if the distance (C) of the crotch-facing innermost second elasticating means of the stomach portion from the corresponding crotch-facing innermost second elasticating means of the back portion is 250 to 420 mm.

The distance of the innermost, crotch-facing second elasticating means from the peripheral contour, bounding the leg openings, of the crotch-side region of the stomach portion and of the back portion that is facing the leg openings is preferably 2-40 mm, more preferably 3-30 mm, particularly preferably 4-15 mm.

Preferably used as first and/or second elasticating means are elasticating means in the form of threads or bands, such as rubber or polyether-polyurethane or polyester-polyurethane threads, preferably elastic threads such as Lycra®, Creora® or Spandex® threads. The first and/or second elasticating means preferably have a thickness of 300-1500 dtex, particularly of 500-900 dtex, more particularly 500-600 dtex. The first and/or second elasticating means are preferably fixed with a pretensioning of 1.5-6.0, particularly of 2.5-5.0 on the chassis-forming shell materials of the stomach portion and back portion. The pretensioning is defined as a factor of the degree of stretching with respect to the unstretched/relaxed state of the elasticating means.

Quite apart from this, it proves to be advantageous if, at least outside the absorbent body, the stomach portion and the back portion are transversely elasticated over the surface area substantially continuously over the longitudinal direction, it also being possible in this way to maintain or realize the advantageous tension conditions.

The absorbent body comprises materials that absorb body fluids, such as natural or synthetic fibers, particularly cellulose fibers, preferably in the form of cellulose fluff. The absorbent core preferably also comprises superabsorbent materials (SAP), particularly based on surface-crosslinked, partially neutralized polyacrylates.

The crotch portion or the longitudinal peripheries of the crotch portion which bound the leg openings are advantageously formed in an arcuately contoured manner.

Further features, details and advantages of the invention are provided by the accompanying patent claims and by the graphic representation and description that follows of a preferred embodiment of the incontinence article according to the invention. In the drawing:

BRIEF DESCRIPTION OF THE DRAWING

FIG. 5 shows a sectional view (schematically) along a transverse center axis of the crotch portion with the sectional plane V-V in FIG. 1;

FIG. 6 shows a perspective view (schematically) of the incontinence article that is shown in FIG. 1 put onto a user;

DESCRIPTION OF THE PREFERRED EMBODIMENT

Figure 1:
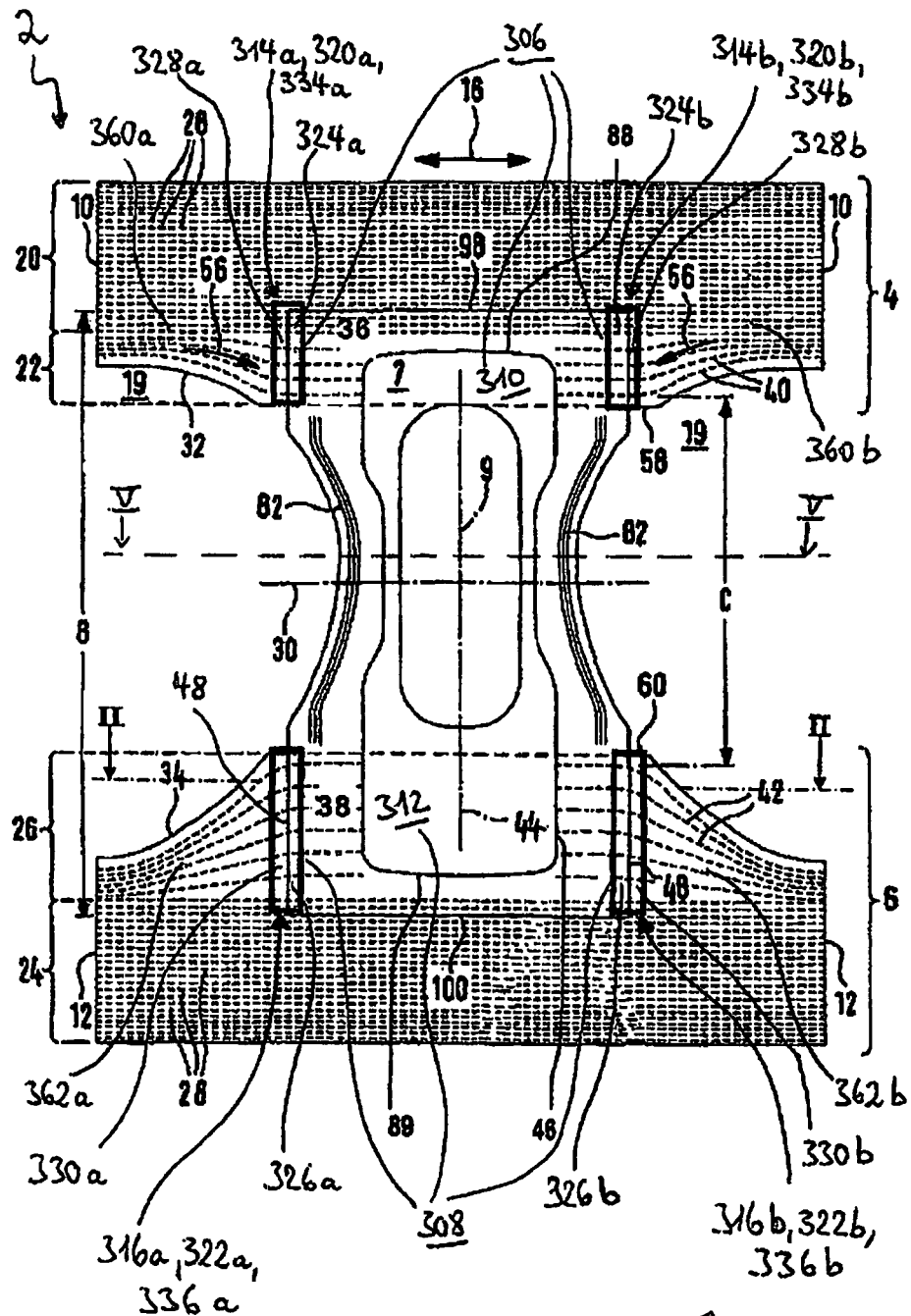
FIG. 1 shows a plan view of an incontinence article according to the invention, wherein a stomach portion, a back portion and a crotch portion connecting the two of the incontinence article have not yet been put together in the form of pants, but are represented in the laid-flat and stretched-out state.

The figures show an incontinence article in the form of pants, designated overall by the reference numeral 2, for receiving solid and liquid body excretions. The incontinence article 2 is formed by three components that can, to the greatest extent, be produced independently of one another, to be specific a front stomach portion 4, a rear back portion 6 and a crotch portion 8, which is arranged between said stomach portion and said back portion and has an absorbent body 7, wherein the crotch portion 8 overlaps with a substantial proportion of the surface area the stomach portion 4 on the one hand and the back portion 6 on the other hand and in the overlapping region is inseparably connected at the manufacturer's. As can be seen from FIG. 1, this leads to an H-shaped basic structure of the incontinence article with a longitudinal direction 9. To form the pants form that is schematically represented in FIG. 6, the joined-together component parts represented in FIG. 1 are then connected to one another, likewise at the manufacturer's, at respective lateral longitudinal peripheral portions 10, 12 of the stomach portion 4 and of the back portion 6, whereby side seam regions 14 (FIG. 6) are formed on both sides. In this state of the incontinence article in the form of pants that is produced at the manufacturer's, the stomach portion 4 and the back portion 6 extend in the transverse or waist-encircling direction 16 continuously up to the side seam regions 14 and thus define a waist opening 18, which is closed in the waist-encircling direction, and leg openings 19, through which the user puts on the incontinence article like a pair of pants.

The stomach portion 4 can be subdivided into a waist-side region 20 and a crotch-side region 22 that is facing the leg openings. A corresponding subdivision is provided in the back portion 6, to be precise likewise into a waist-side region 24 and a crotch-side region 26 that is facing the leg openings.

Provided in the waist-side region 20 of the stomach portion 4 and in the waist-side region 24 of the back portion 6 are first elasticating means 28, which may particularly be elasticating means in the form of threads, such as Lycra® threads, which in the pre-stretched state, are connected to the flat materials (chassis materials) of the stomach portion 4 and of the back portion 6, in what is known as the stretch-bonding process. These first elasticating means 28 extend in the transverse or waist-encircling direction 16 from one side seam region 14 to the other.

The crotch-side portion 22, facing the leg openings 19, of the stomach portion 4 and the equivalent portion 26 of the back portion 6 have a peripheral contour 32 and 34, respectively, deviating from the transverse or waist-encircling direction 16 and running in the direction of a transverse center axis 30 of the crotch portion 8. In the representation that is shown in FIG. 1, this peripheral contour 32, 34 is also arcuate, and therefore suitable for bounding the leg openings 19. The shape of the crotch-side region 22 or that is facing the leg openings also creates a relatively great overlapping region 36, 38 between the crotch portion 8 and the stomach portion 4 or the back portion 6, which is essential with regard to a tear-resistant connection of the crotch portion 8 and the stomach portion 4 or the back portion 6.

Figure 7:
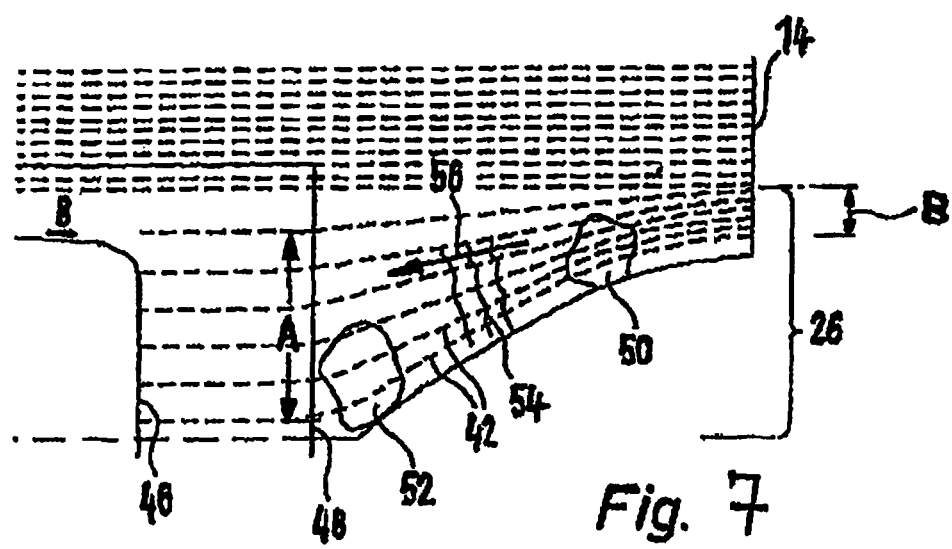
FIG. 7 shows a representation of the incontinence article that is shown in FIG. 1 in the form of a detail.

The respective crotch-side region 22, 26 that is facing the leg openings 19 of the stomach portion 4 and of the back portion 6 is likewise of an elasticated form. Respectively provided there are second elasticating means 40 and 42. The second elasticating means 40, 42 in each case extend from the side seam regions 14 in the direction of a longitudinal center axis 44 of the incontinence article. As can be seen from FIGS. 1 and 7, the second elasticating means 40, 42 fan out in the direction of the longitudinal center axis 44. This means that the spacing between them increases in the direction of the longitudinal center axis 44. This fanning out of the second elasticating means 40 and 42 can also be quantitatively specified more precisely on the basis of FIG. 7. For example, the second elasticating means 42 of the back portion 6 that are represented in FIG. 7 have in the side seam regions 14 a minimum distance from one another of 3 to 8 mm (spacing of elasticating means lying directly next to one another) and at a periphery 46 of the absorbent body or a longitudinal periphery 48 of the crotch portion 8 a maximum distance (spacing of elasticating means lying directly next to one another) from one another of 7 to 35 mm. On the basis of FIG. 7, a degree of fanning out F can also be defined as follows:

$$F=(A-B)/B*100\%.$$

This degree of fanning out may advantageously lie between 50 and 900%, particularly between 100 and 700% and more particularly between 150 and 550%. It is advantageously greater in the back portion 6 than in the stomach portion 4. The variables A and B are defined here as the distance of the outermost second elasticating means 40, 42 in the longitudinal direction 9 from the innermost second elasticating means 40, 42 in the longitudinal direction 9 (that is to say not the spacing of elasticating means lying directly next to one another), to be precise A as the maximum distance, particularly at the longitudinal periphery 48 of the crotch portion 8, and B as the minimum distance, particularly in the side seam region 14 (cf. FIG. 7).

If the degree of fanning out is chosen to be sufficient in the case of the second elasticating means 40, 42, a decreasing restoring force can in this way be realized within the crotch-side region 22 or 26 that is facing the leg openings 19, as long as it is ensured that the arcuate shape of the second elasticating means 40, 42 that is facing away from the waist or transverse direction 16 does not cause an excessive increase in the pretensioning as a result of the greater path followed by these second elasticating means 40, 42. If an area 50 of the crotch-side region 22 or 26 concerned that is lying nearer the side seam region 14 is considered along with an area 52 that is lying nearer the crotch portion 8, the restoring force that occurs under stretching over the surface area of the area 52 (stretching in the direction of the elasticating means 42) is less than the restoring force that occurs under stretching of the area 50. This advantageously also has the effect that, as a result of the lower elastic forces that are exerted by the second elasticating means 40, 42 in the case represented by way of example, the chassis materials of the stomach portion 4 and of the back portion 6 are gathered to a lesser extent, so that a smaller number of folds/ruffles 54 occur, to be precise from the respective side seam region 14 in the direction of the crotch portion 8. The fact that the restoring forces occurring under stretching over the surface area of the stomach portion in the crotch-side region 22 that is facing the leg openings of the stomach portion 4 or the equivalent portion 26 of the back portion 6 decrease in the direction of the arrow 56, that is to say generally from the side seam region 14 in the direction of the crotch portion 8, means that a considerable improvement in the wearing comfort is achieved, because—as has been established—elastically stretchable materials prove to be particularly problematic in precisely these regions, because these materials are especially subjected to pulling and stretching in a way corresponding to the physiognomy of the human anatomy in these regions. A deliberately and advantageously provided reduction in this restoring force, that is to say decreasing restoring force in the direction of the arrow 56, that is in the direction of increasing proximity to the crotch portion 8, has the effect here of providing a hitherto unachieved degree of freedom.

Figure 8:
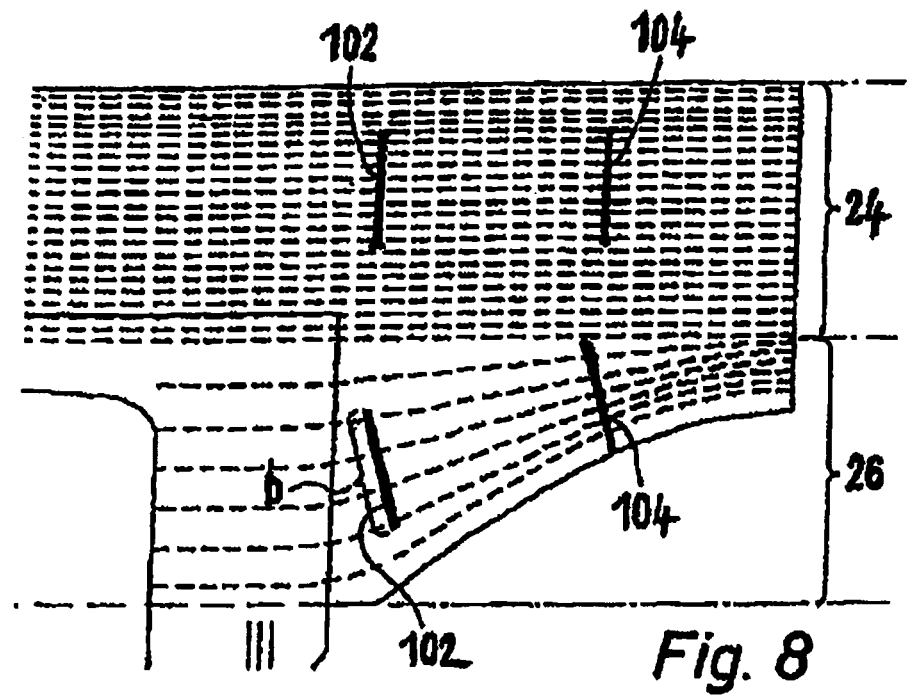
FIGS. 8, 9 illustrate by way of example the determination of restoring forces in the stomach portion and back portion of the incontinence article.
Figure 9:
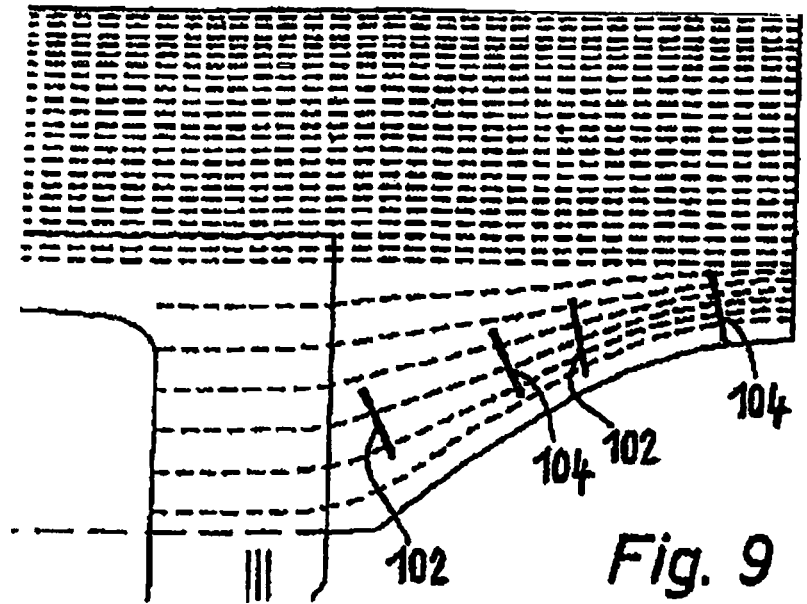

As stated at the beginning, restoring forces may be determined directly on the chassis of the incontinence article. For this, the region concerned of the stomach portion 4 or of the back portion is clamped between two clamping jaws 102, 104 (see FIGS. 8, 9) of a defined, identical clamping jaw width (b), and restoring forces then determined under defined stretching of the regions to be measured that simulates the state of use, by particularly 30% or 50% or 80% of the initial length (of the clamping jaw spacing in the unclamped state). The clamping jaws 102, 104 are in this case respectively moved away from one another. The clamping jaws 102, 104 should fix as many elasticating means 40, 42 as possible, but at least two arranged next to one another, of the region to be measured and they should be oriented substantially perpendicularly with respect to the line followed by the elasticating means, so that the stretching between the clamping jaws 102, 104, that is to say the moving apart of the clamping jaws 102, 104, takes place substantially in the direction of the line followed by the elasticating means. This is realized in FIGS. 8 and 9.

In the case of the preferred embodiment of the incontinence article 2 that is represented, a distance C of the crotch-facing innermost second elasticating means 40 of the stomach portion 4 from the corresponding crotch-facing innermost second elasticating means 42 of the back portion 6 is between 250 and 420 mm, depending on the manufactured size of the incontinence article. The second elasticating means 40, 42 extend substantially up to the crotch-facing transverse periphery 58, 60 of the stomach portion 4 and of the back portion 6. The distance between the stomach portion 4 and the back portion 6 is 250-400 mm.

The distance of the innermost, crotch-facing second elasticating means 40, 42 from the peripheral contour 32, 34, bounding the leg openings, of the crotch-side region 22, 26 of the stomach portion 4 and of the back portion 6 that is facing the leg openings is preferably 2-40 mm, more preferably 3-30 mm, particularly preferably 4-15 mm.

The extent of the stomach portion 4 and of the back portion 6 in the side seam region 14 in the longitudinal direction 9 is advantageously between 100 and 220 mm. The extent of the crotch portion 8 in the transverse direction 16 is advantageously 200 to 350 mm.

Figure 2:
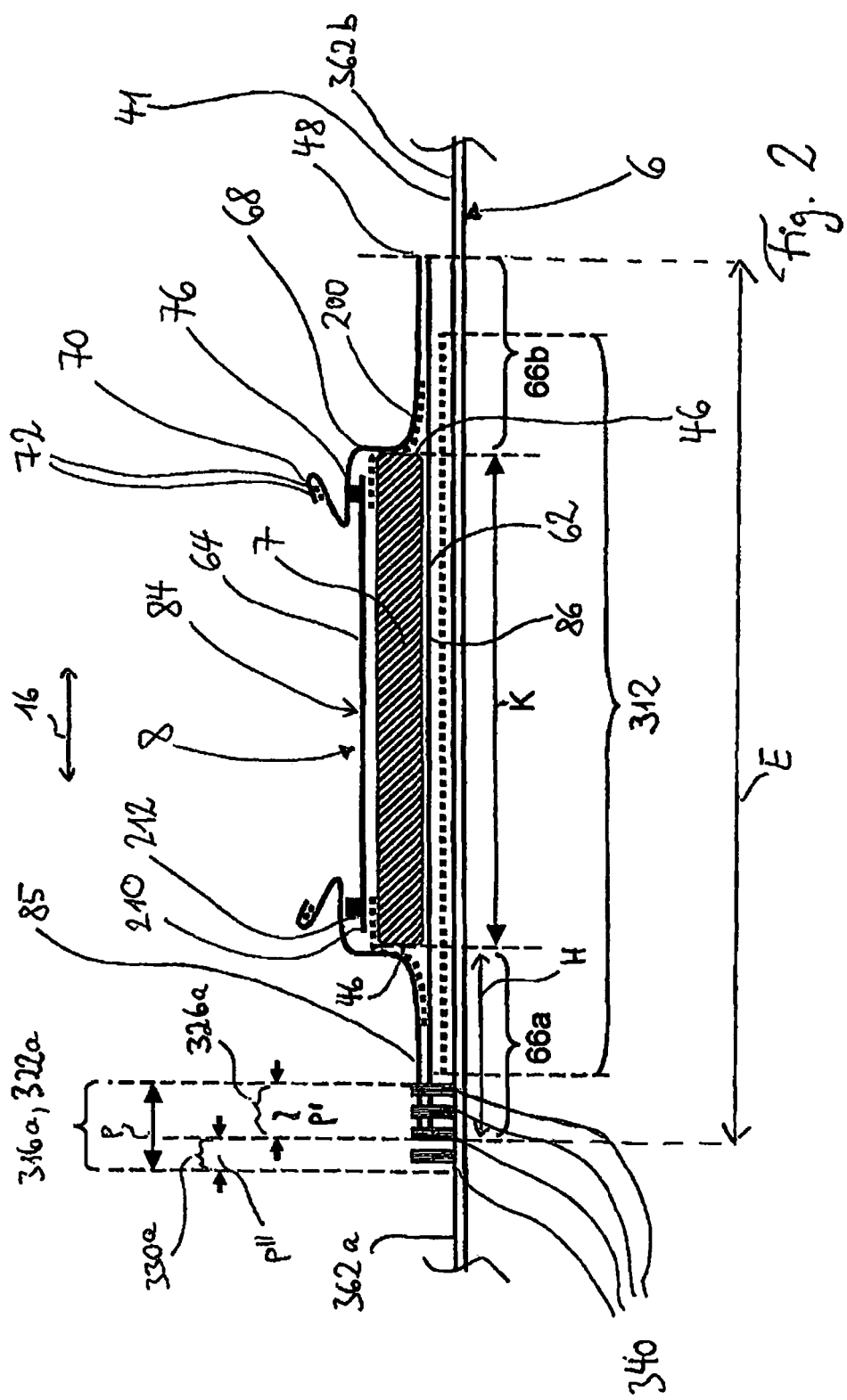
FIG. 2 shows a sectional view (schematically) along a transverse center axis of the crotch portion and back portion attached thereto with the sectional plane II-II in FIG. 1.

As can be seen in FIG. 2, which schematically represents a sectional view along the sectional plane II-II from FIG. 1, the crotch portion 8 comprises a liquid-impermeable backsheet material 62, which may be formed particularly by a breathable, but liquid-impermeable sheeting material, and a topsheet material 84, preferably produced on a nonwoven basis, which is a composite of a topsheet material 64 produced on a nonwoven basis and barrier means 68 arranged on both sides. As can be seen from FIG. 2, arranged between the backsheet material and the topsheet material is the absorbent body 7. The absorbent body 7 has longitudinal peripheries 46. In the case represented by way of example, the backsheet material 62 respectively forms an overhang 66a, 66b in the transverse direction 16 on both sides of the longitudinal peripheries 46. The topsheet 64 protrudes only relatively slightly beyond the absorbent body 7 in the transverse direction; however, an upright barrier means 68 is respectively provided, running on both sides of the absorbent body 7 in the longitudinal direction 9, typically referred to as an upright cuff element or leg-band element and preferably formed by a hydrophobic, particularly liquid-impermeable nonwoven material, which extends in the transverse direction 16 preferably up to the lateral longitudinal peripheries 48 of the crotch portion 8. The barrier means 68 is in this case joined onto the longitudinal peripheries 210 or the longitudinal peripheral regions 212 of the topsheet material 64 at joining locations 76. The distal ends 70 of the barrier means 68 are provided with further elasticating means 72, which raise the barrier means 68 against the surface of the user's skin during use of the incontinence article, as is represented in FIG. 5, a schematic sectional view along the sectional plane IV-IV from FIG. 1. The joining locations 76 arranged in the longitudinal direction 9 form the continuously extended cuff base line 80.

It proves to be particularly advantageous here if the mentioned overhang 66a, 66b of the backsheet material 62 and/or of the topsheet material 84 on both sides of the longitudinal peripheries 46 of the absorbent body 7, that is to say in total, is at least 25% with respect to the greatest width E of the crotch portion 8. This is because in this way there is space in the transverse direction 16 for the arrangement of leg elasticating means 82 to extend along the leg openings 19. This is because it proves to be advantageous if the leg elasticating means 82 run at a certain distance from the bulky, and consequently rather rigid, absorbent body 7, in order on the one hand not to exert any additional stretching or torsional forces on the absorbent body, which could adversely influence its absorption behavior, and on the other hand to realize a liquid-tight leg termination that is largely uninfluenced by the absorbent body. It proves to be particularly advantageous in the case represented that these leg elasticating means 82 end in the longitudinal direction 9 at a clear distance of particularly at least 10 mm, preferably at least 20 mm, before the second elasticating means 40 and 42 of the stomach portion 4 or of the back portion 6. Preferably, these leg elasticating means 82 end in the longitudinal direction 9 before the stomach portion 4 and the back portion 6. This is advantageous and essential because the leg elasticating means 82 in this way have little or no influence on the tension-related behavior of the stomach portion 4 and of the back portion 6. This is because it has been recognized that it proves to have an adverse effect on the aim to be advantageously achieved of improving the wearing comfort precisely in the crotch-side region 22 and 26 of the stomach portion and of the back portion 6 that is facing the leg openings 19 if the leg elasticating means 82, which are usually formed with great pretensioning and a correspondingly great restoring force, additionally run there.

As can be seen from FIG. 2 in conjunction with FIG. 1, in the case of the crotch portion 8 a relatively great overhang 66a, 66b in the transverse direction 16 is realized on both sides of the longitudinal peripheries 46 of the absorbent body 7, to be precise in particular also at regions of the crotch portion 8 that are facing the stomach portion 4 and the back portion 6, respectively. As a result—as already pointed out—a relatively great overlapping region 36, 38 of the crotch portion 8 with the stomach portion 4 and with the back portion 6 is realized. According to a preferred configurational variant, the overlapping region 36 of the crotch portion 8 with the stomach portion 4 comprises at least 12% of the surface area of the stomach portion 4, and the overlapping region 38 of the crotch portion 8 with the back portion 6 comprises at least 20% of the surface area of the back portion 6. This proves to be advantageous since secure fixing of the crotch portion 8 to the stomach portion 4 and to the back portion 6 can be achieved in this way.

FIG. 1 shows an incontinence article 2 with an H-shaped basic structure in its flat spread-out state.

As can be seen in FIG. 1, the incontinence article 2 has the first joining regions 310, 312 and second joining regions 314a, 314b, 316a, 316b according to the invention, which are arranged in the front and rear overlapping regions 36, 38, and consequently provide a front and a rear connecting region 306, 308, in which the crotch portion 8 is inseparably joined onto the stomach portion 4 and the back portion 6, respectively. Together with FIG. 2, which represents a schematic sectional view along the plane II-II from FIG. 1 (although only the second joining region on the left side is schematically depicted here), it is clear that the second joining region 314a, 314b, 316a, 316b is in this case arranged in a region 320a, 320b, 322a, 322b bridging the respective longitudinal periphery 48 of the crotch portion 8. Consequently, both a subregion 324a, 324b, 326a, 326b of the overhang 66a, 66b and a subregion 328a, 328b, 330a, 330b of the stomach portion 4 or back portion 6 that is adjacent the longitudinal periphery 48 is respectively extended over by the second joining region 314a, 314b, 316a, 316b with the joining means 340 arranged therein.

These second joining regions 314a, 314b, 316a, 316b in each case form a reinforcing region 334a, 334b, 336a, 336b.

The second joining regions 314a, 314b, 316a, 316b, and consequently the reinforcing regions 334a, 334b, 336a, 336b, extend, when considered in the longitudinal direction 9, from the crotch-facing transverse periphery 58, 60 of the stomach portion 4 and of the back portion 6 continuously in the direction of the longitudinal ends of the crotch portion, preferably to at least a respective longitudinal end 98, 100 of the crotch portion 8.

The second joining regions 314a, 314b, 316a, 316b have an overall width P of preferably 5-60 mm, particularly of 10-50 mm, particularly of 10-40 mm, more particularly 10-30 mm.

In the subregion 324a, 324b, 326a, 326b of the respective overhang 66a, 66b that is extended over by the second joining region 314a, 314b, 316a, 316b, the second joining region has a width P' of preferably greater than 1 mm, more preferably greater than 2 mm, more preferably greater than 5 mm but preferably less than 60 mm, more preferably less than 50 mm, more preferably less than 40 mm, more preferably less than 30 mm, more preferably less than 20 mm, particularly preferably of 10 mm.

The second joining region 314a, 314b, 316a, 316b extends over the respective subregion 324a, 324b, 326a, 326b of the overhang 66a, 66b in the transverse direction in such a way that the proportion P'/H of the subregion 324a, 324b, 326a, 326b of the respective overhang 66a, 66b that is extended over by the second joining region 314a, 314b, 316a, 316b, with the width P' with respect to the respective overhang 66a, 66b with the width H is preferably at least 0.01, particularly at least 0.04, more particularly preferably at least 0.07, more particularly at least 0.10, but preferably at most 0.90, more particularly at most 0.80, more particularly at most 0.70, more particularly at most 0.60, more particularly at most 0.50, more particularly at most 0.40.

In the subregion 328a, 328b, 330a, 330b of the stomach portion 4 or back portion 6 that is extended over by the second joining region 314a, 314b, 316a, 316b, the second joining region has a width P''' preferably greater than 1 mm, more preferably greater than 2 mm, more preferably greater than 5 mm but preferably less than 60 mm, more preferably less than 50 mm, more preferably less than 40 mm, more preferably less than 30 mm, more preferably less than 20 mm, particularly preferably of 10 mm.

The second joining region 314a, 314b, 316a, 316b extends over the respective subregion 328a, 328b, 330a, 330b of the stomach portion 4 and of the back portion 6 in the transverse direction 16 in such a way that the proportion P'''/H of the respective subregion 328a, 328b, 330a, 330b of the stomach portion and back portion that is extended over by the second joining region 314a, 314b, 316a, 316b, with the width P''' with respect to the respective overhang 66a, 66b with the width H, is preferably at least 0.01, particularly at least 0.04, more particularly at least 0.07, more particularly at least 0.10, but preferably at most 0.90, particularly at most 0.80, more particularly at most 0.70, more particularly at most 0.60, more particularly at most 0.50 and more particularly at most 0.40.

Figure 10:
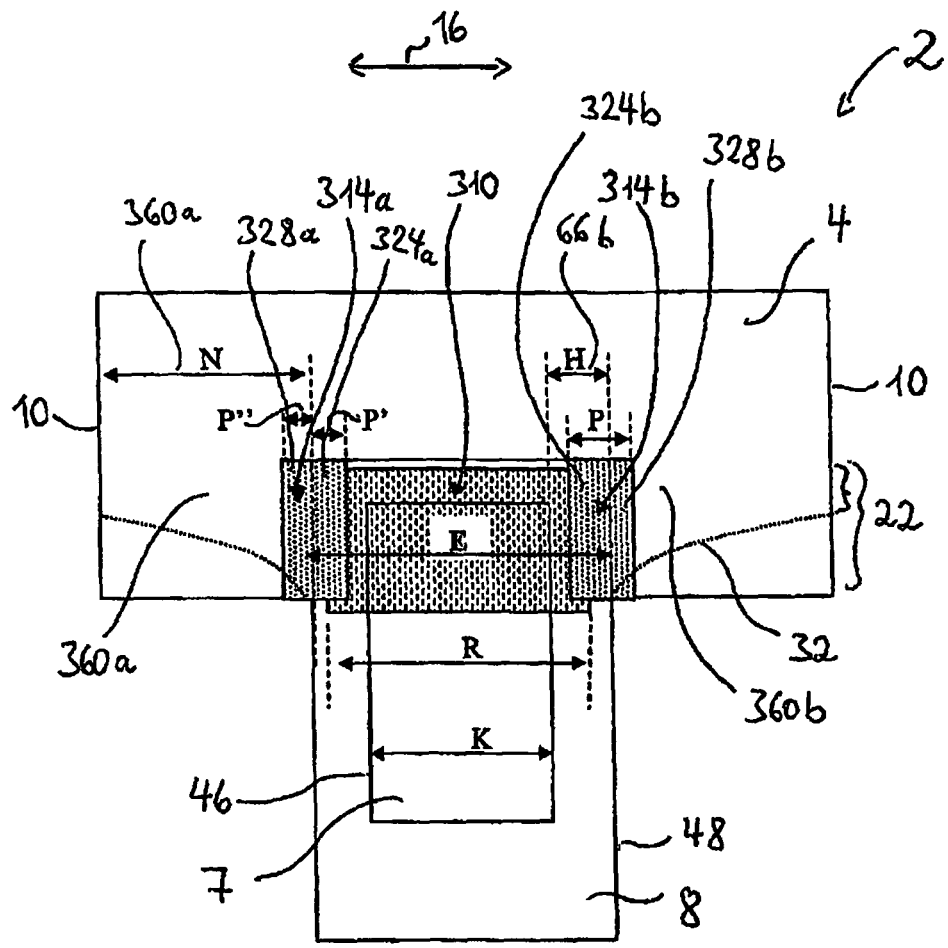
FIG. 10 shows a plan view of a schematically represented incontinence article in the laid-flat and stretched-out state, wherein the crotch portion is shown initially only connected to a stomach portion.

As, explained above, the second joining region 314a, 314b, 316a, 316b extends over an adjacent subregion 328a, 328b, 330a, 330b of the stomach portion and of the back portion. Between the longitudinal periphery 48 of the crotch portion 8 and the longitudinal peripheral portion 10, 12 of the stomach portion 4 and back portion 6 are the respective side regions 360a, 360b, 362a, 362b. The respective side region has a width N. As also schematically represented in FIG. 10, the respective side region 360a, 360b (and 362a, 362b, respectively) of the stomach portion and of the back portion with the width N is extended over by the second joining region 314a, 314b (and 316a, 316b, respectively) with the proportionate width P'''. In FIG. 10, the stomach portion or back portion is represented as a rectangular panel. However, as represented in FIG. 1 and also as depicted by dashed lines in FIG. 10, the region 22 facing the crotch may also assume an arcuate peripheral contour 32.

The proportion P'''/N of the respective subregion 328a, 328b, 330a, 330b of the stomach portion and/or back portion that is extended over by the second joining region 314a, 314b, 316a, 316b, with the width P''' with respect to the respective side region 360a, 360b, 362a, 362b of the stomach portion and/or back portion with the width N, is preferably at least 0.01, particularly at least 0.015, more particularly at least 0.020, and preferably at most 0.35, particularly at most 0.30, more particularly at most 0.25, more particularly at most 0.20, more particularly at most 0.15, more particularly at most 0.10.

In an advantageous way, the proportion P'/N of the respective subregion 324a, 324b, 326a, 326b of the respective overhang 66a, 66b that is extended over by the second joining region 314a, 314b, 316a, 316b, with the width P' with respect to the respective side region 360a, 360b, 362a, 362b of the stomach portion and/or back portion with the width N, is preferably at least 0.01, particularly at least 0.015, more particularly at least 0.020 and preferably at most 0.35, particularly at most 0.30, more particularly at most 0.25, more particularly at most 0.20, more particularly at most 0.15, more particularly at most 0.10.

The joining means 340 arranged in the second joining region 314a, 314b, 316a, 316b (FIG. 2) are welding locations, preferably ultrasonic welding locations, which are not arranged over the full surface area within the second joining region.

Figure 3:
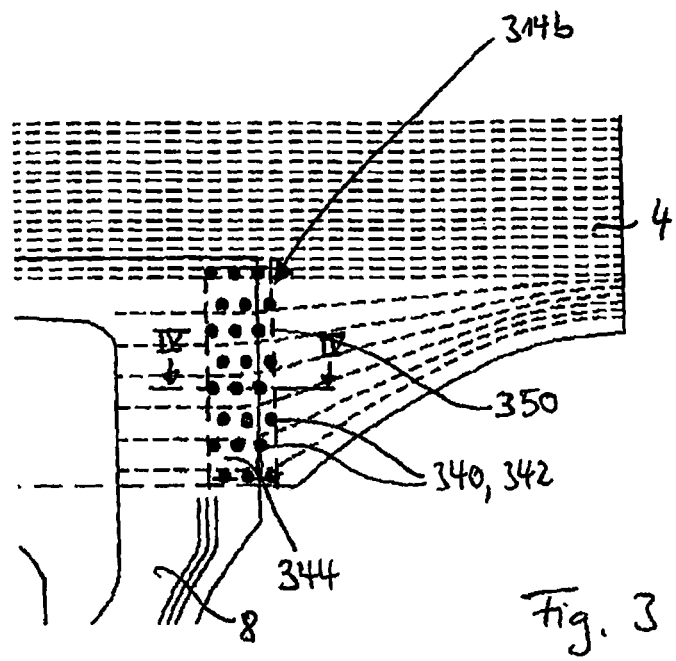
FIG. 3 shows a representation of a second joining region of the incontinence article that is shown in FIG. 1 in the form of a detail.

As also represented in FIG. 3 (here a detail of the incontinence article with the attachment of the crotch portion 8 to the stomach portion 4), the joining means 340 are arranged in a puntiform manner. The joining means 340 in the form of ultrasonic welding locations in each case form a joining location (that is to say an attached region) 342, which is spaced apart from the next joining location by an unattached region 344. To determine the areal extent of a second joining region (here 314b); the respectively outermost joining means 340 or joining locations 342 are connected by means of an imaginary line 350. The joining means 340 arranged in a point pattern form in the overall surface area that is extended over by the second joining region 314b attached surface areas (joining locations) which, in total, assume preferably at least 1.5%, particularly at least 2.0%, more particularly at least 2.3%, more particularly at least 2.5% and preferably at most 20.0%, particularly at most 15.0%, more particularly at most 10.0%, more particularly at most 8.0%, more particularly at most 7.0%, more particularly at most 6.0%, with respect to the overall surface area extended over by the second joining region. The individual joining means have a diameter preferably of at least 0.2 mm, particularly of at least 0.3 mm, more particularly of at least 0.4 mm and preferably of at most 2.5 mm, particularly at most 2.0 mm, more particularly at most 1.5 mm, more particularly at most 1.2 mm, more particularly at most 1.0 mm. The neighboring individual joining means 340 present in the point pattern are spaced apart from one another by preferably 1-10 mm, particularly by 1-8 mm, more particularly by 1-6 mm, more particularly by 1-5 mm, more particularly by 1.5-4.5 mm, more particularly by 2-4 mm.

Figure 4:
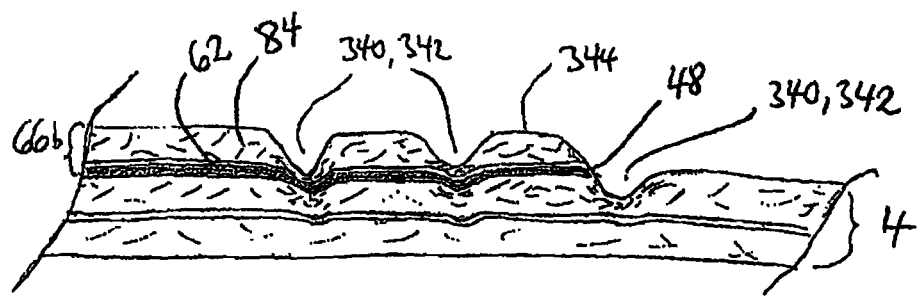
FIG. 4 shows a sectional view (schematically) of the second joining region with the sectional plane IV-IV in FIG. 3.

FIG. 4 represents a sectional view of the second joining region 314a along the sectional plane IV-IV from FIG. 3.

The overhang 66b of the crotch portion 8, consisting of a topsheet material 84 of nonwoven and a backsheet 62 of sheeting, is attached to the stomach portion 4 lying thereunder by means of joining locations 342 produced by the joining means 340.

As represented in FIG. 2, the first joining region 312 runs beneath the absorbent body 7 with the width K, therefore also extends over the contour, that is to say the respective longitudinal periphery 46 of the absorbent body 7, but not outside the contour of the crotch portion 8, but instead ends within the longitudinal peripheries 48 of the crotch portion 8. The crotch portion 8 is in this case preferably connected to the back portion 6 by means of an application of adhesive over the full surface area.

As in the present example, the topsheet material is a composite of a topsheet 64 and barrier means 68 joined onto the longitudinal peripheries 210 or the longitudinal peripheral regions 212 on both sides of the topsheet 64. The topsheet material is in this case attached by means of an adhesive 200, particularly a hotmelt adhesive, to the absorbent body and, overlapping the side periphery 46 of the absorbent body 7, also to an adjacent subregion of the backsheet material 62.

A separate joining means (not represented in FIG. 2) is also provided between the backsheet material and the absorbent body and between the topsheet material and the absorbent body. These separate joining means are applied in the form of an adhesive, not over the full surface area but in the form of an interrupted pattern. These separate joining means, provided in the form of an adhesive, are therefore applied for example in grid form, strip form or as a spiral pattern.

FIG. 10 schematically shows a not yet completed incontinence article 2 with a stomach portion 4 joined onto the crotch portion 8 and an advantageous configuration of the arrangement of the first joining region 310 and of the respectively second joining regions 314a, 314b. As represented in FIG. 10, the first joining region 310 extends in the transverse direction 16 with the width R advantageously over the longitudinal peripheries 46 of the absorbent body 7 with a width K, but without reaching over the longitudinal peripheries 48 of the crotch portion 8. The respectively second joining region 314a, 314b with the width P in each case bridges the longitudinal periphery 48 of the crotch portion 8. The joining region 314a, 314b thereby respectively extends over an adjacent subregion 324a, 324b of the overhang 66a, 66b with the width H, to be precise with the width P'. The second joining region 314a, 314b also respectively extends over an adjacent subregion 328a, 328b of the stomach portion 4, to be precise with the width P'''. The first joining region 310 thereby extends in the transverse direction in such a way that an overlap with the respective second joining region 324a, 324b is obtained.

I claim:

1. An incontinence article in pants form for receiving body excretions, the article comprising:
    a front stomach portion;
    a rear back portion;
    a crotch portion comprising an absorbent body, said crotch portion having an inner side, an outer side as well as longitudinal peripheries and longitudinal ends, said crotch portion thereby extending in a longitudinal direction between said stomach Portion and said back portion, wherein each of said stomach portion and said back portion has an inner side and a crotch-facing transverse periphery, said crotch portion thereby overlapping with said stomach portion in a front overlapping region and with said back portion in a rear overlapping region, said crotch portion further comprising a liquid-impermeable backsheet material and a topsheet material between which said absorbent body is disposed, said absorbent body also having longitudinal peripheries, at least one of said topsheet material and said backsheet material forming an overhang extending beyond said longitudinal periphery of said absorbent body;
    two side seams generated by connecting together said stomach portion and said back portion by a manufacturer of the article on both sides thereof, said front stomach portion and said rear back portion thereby forming a stomach and back band which is continuous in a transverse or waist-encircling direction and defining a waist opening that is closed in said waist-encircling direction, wherein said crotch portion, said stomach portion and said back portion thereby also define leg openings of the incontinence article;
    first elasticating means disposed in said stomach portion and said back portion, spaced apart from one another and extending parallel to one another in said transverse or waist-encircling direction to thereby elasticize said stomach portion and said back portion over surface areas thereof;
    second elasticating means disposed in a crotch-side region of said stomach portion and of said back portion facing said leg openings;
    a front connecting region disposed, structured and dimensioned to inseparably join said outer side of said crotch portion to said inner side of said stomach portion; and a rear connecting region disposed, structured and dimensioned to inseparable join said outer side of said crotch portion to said inner side of said back portion, wherein said front and rear connecting regions of said stomach portion and of said back portion each respectively comprise a first joining region and second joining regions, said respective first joining region extending, at least in certain portions, beneath said absorbent body, wherein said second joining regions are disposed to bridge a respective said longitudinal periphery of said crotch portion and to extend over both a subregion of said overhang of said crotch portion and a subregion adjacent thereto of said stomach portion and/or of said back portion, a respective said second joining region extending in said longitudinal direction from a respective said crotch-facing transverse periphery of said stomach portion and/or said back portion towards said longitudinal ends of said crotch portion, said second joining regions being formed by joining means structured as welding locations, ultrasonic welding locations, thermal welding locations and/or calender welding, locations, thereby forming reinforcing regions, wherein a ratio P'/H of a subregion of a respective said overhang that is extended over by said second joining region and having a width (P'), to a respective said overhang with a width (H) in said front and/or said rear overlapping region, is at least 0.01, at least 0.04, at least 0.07, at least 0.10, at most 0.90, at most 0.80, at most 0.70, at most 0.60, at most 0.50 or at most 0.40.

2. The incontinence article of claim 1, wherein said second joining regions and said reinforcing regions extend, as viewed in said longitudinal direction, from said crotch-facing transverse periphery of said stomach portion and of said back portion to at least a respective said longitudinal end of said crotch portion.

3. The incontinence article of claim 1, wherein a respective second joining region with an overall width P is arranged along said longitudinal periphery of said crotch portion in such a way that a ratio of the width P' to the width P''' is preferably between 1:4 and 4:1, between 1:3 and 3:1, between 1:2 and 2:1 or 1:1, wherein P' is a width of said subregion extended over by said second joining region.

4. The incontinence article of claim 1, wherein said second joining region is disposed parallel to said longitudinal direction and has a constant overall width.

5. The incontinence article of claim 1, wherein joining means in said second joining region are arranged in a point pattern and a sum of a surface area attached by said joining means assumes a proportion of at least 1.5%, at least 2.0%, at least 2.3%, at least 2.5%, at most 20.0%, at most 15.0%, at most 10.0%, at most 8.0%, at most 7.0% or at most 6.0%, with respect to an overall surface area extended over by said second joining region.

6. The incontinence article of claim 1, wherein said overhang of said backsheet material and/or of said topsheet material in said transverse direction summed over both sides of said longitudinal peripheries of said absorbent body, is at least 25%, 25-50%, 30-45% and or 35-45% of a greatest width (E) of said crotch portion.

7. An incontinence article in pants form for receiving body excretions, the article comprising:
   a front stomach portion;
   a rear back portion;
   a crotch portion comprising an absorbent body, said crotch portion having an inner side, an outer side as well as longitudinal peripheries and longitudinal ends, said crotch portion thereby extending in a longitudinal direction between said stomach portion and said back portion, wherein each of said stomach portion and said back portion has an inner side and a crotch-facing transverse periphery, said crotch portion thereby overlapping with said stomach portion in a front overlapping region and with said back portion in a rear overlapping region, said crotch portion further comprising a liquid-impermeable backsheet material and a topsheet material between which said absorbent body is disposed, said absorbent body also having longitudinal peripheries, at least one of said topsheet material and said backsheet material forming an overhang extending beyond said longitudinal periphery of said absorbent body;
   two side seams generated by connecting together said stomach portion and said back portion by a manufacturer of the article on both sides thereof, said front stomach portion and said rear back portion thereby forming a stomach and back band which is continuous in a transverse or waist-encircling direction and defining a waist opening that is closed in said waist-encircling direction, wherein said crotch portion, said stomach portion and said back portion thereby also define leg openings of the incontinence article;
   first elasticating means disposed in said stomach portion and said back portion, spaced apart from one another and extending parallel to one another in said transverse or waist-encircling direction to thereby elasticize said stomach portion and said back portion over surface areas thereof;
   second elasticating means disposed in a crotch-side re-ion of said stomach portion and of said back portion facing said leg openings;
   a front connecting region disposed, structured and dimensioned to inseparably join said outer side of said crotch portion to said inner side of said stomach portion; and
   a rear connecting region disposed, structured and dimensioned to inseparable join said outer side of said crotch portion to said inner side of said back portion, wherein said front and rear connecting regions of said stomach portion and of said back portion each respectively comprise a first joining region and second joining regions, said respective first joining region extending, at least in certain portions, beneath said absorbent body, wherein said second joining re ions are disposed to bride a respective said longitudinal periphery of said crotch portion and to extend over both a subregion of said overhang of said crotch portion and a subregion adjacent thereto of said stomach portion and/or of said back portion, a respective said second joining region extending in said longitudinal direction from a respective said crotch-facing transverse periphery of said stomach portion and/or said back portion towards said longitudinal ends of said crotch portion, said second joining regions being formed by joining means structured as welding locations, ultrasonic welding locations, thermal welding locations and/or calender welding locations, thereby forming reinforcing regions, wherein a ratio P''/H of a respective subregion of said stomach portion and/or of said back portion that is extended over by said second joining region with a width (P''), to a respective overhang with a width (H), is at least 0.01, at least 0.04, at least 0.07, at least 0.10, at most 0.90, at most 0.80, at most 0.70, at most 0.60, at most 0.50 or at most 0.40.

8. The incontinence article of claim 7, wherein said second joining regions and said reinforcing regions extend, as viewed in said longitudinal direction, from said crotch-facing transverse periphery of said stomach portion and of said back portion to at least a respective said longitudinal end of said crotch portion.

9. The incontinence article of claim 7, wherein a respective second joining region with an overall width P is arranged along said longitudinal periphery of said crotch portion in such a way that a ratio of the width P' to the width P''' is preferably between 1:4 and 4:1, between 1:3 and 3:1, between 1:2 and 2:1 or 1:1, wherein P' is a width of said subregion extended over by said second joining region.

10. The incontinence article of claim 7, wherein said second joining region is disposed parallel to said longitudinal direction and has a constant overall width.

11. The incontinence article of claim 7, wherein joining means in said second joining region are arranged in a point pattern and a sum of a surface area attached by said joining means assumes a proportion of at least 1.5%, at least 2.0%, at least 2.3%, at least 2.5%, at most 20.0%, at most 15.0%, at most 10.0%, at most 8.0%, at most 7.0% or at most 6.0%, with respect to an overall surface area extended over by said second joining region.

12. The incontinence article of claim 7, wherein said overhang of said backsheet material and/or of said topsheet material in said transverse direction summed over both sides of said longitudinal peripheries of said absorbent body, is at least 25%, 25-50%, 30-45% and or 35-45% of a greatest width (E) of said crotch portion.

13. An incontinence article in pants form for receiving body excretions, the article comprising:
    a front stomach portion;
    a rear back portion:
    a crotch portion comprising an absorbent body, said crotch portion having an inner side, an outer side as well as longitudinal peripheries and longitudinal ends, said crotch portion thereby extending in a longitudinal direction between said stomach portion and said back portion, wherein each of said stomach portion and said back portion has an inner side and a crotch-facing transverse periphery, said crotch portion thereby overlapping with said stomach portion in a front overlapping region and with said back portion in a rear overlapping region, said crotch portion further comprising a liquid-impermeable backsheet material and a topsheet material between which said absorbent body is disposed, said absorbent body also having longitudinal peripheries, at least one of said topsheet material and said backsheet material forming an overhang extending beyond said longitudinal periphery of said absorbent body;
    two side seams generated by connecting together said stomach portion and said back portion by a manufacturer of the article on both sides thereof, said front stomach portion and said rear back portion thereby forming a stomach and back band which is continuous in a transverse or waist-encircling direction and defining a waist opening that is closed in said waist-encircling direction, wherein said crotch portion, said stomach portion and said back portion thereby also define leg openings of the incontinence article;
    first elasticating means disposed in said stomach portion and said back portion, spaced apart from one another and extending parallel to one another in said transverse or waist-encircling direction to thereby elasticize said stomach portion and said back portion over surface areas thereof;
    second elasticating means disposed in a crotch-side region of said stomach portion and of said back portion facing said leg openings;
    a front connecting region disposed, structured and dimensioned to inseparably join said outer side of said crotch portion to said inner side of said stomach portion; and
    a rear connecting region disposed, structured and dimensioned to inseparable join said outer side of said crotch portion to said inner side of said back portion, wherein said front and rear connecting regions of said stomach portion and of said back portion each respectively comprise a first joining region and second joining regions, said respective first joining region extending, at least in certain portions, beneath said absorbent body, wherein said second joining regions are disposed to bridge a respective said longitudinal periphery of said crotch portion and to extend over both a subregion of said overhang of said crotch portion and a subregion adjacent thereto of said stomach portion and/or of said back portion, a respective said second joining region extending in said longitudinal direction from a respective said crotch-facing transverse periphery of said stomach portion and/or said back portion towards said longitudinal ends of said crotch portion, said second joining regions being formed by joining means structured as welding locations, ultrasonic welding locations, thermal welding locations and/or calender welding locations, thereby forming reinforcing regions, wherein a ratio P''/N of a respective subregion of said stomach portion and/or of said back portion that is extended over by said second joining region with a width (P''), to a respective side region of the stomach portion and/or of said back portion with a width (N), is at least 0.01, at least 0.015, at least 0.020, at most 0.35 at most 0.30, at most 0.25, at most 0.20, at most 0.15 or at most 0.10.

14. The incontinence article of claim 13, wherein said second joining regions and said reinforcing regions extend, as viewed in said longitudinal direction, from said crotch-facing transverse periphery of said stomach portion and of said back portion to at least a respective said longitudinal end of said crotch portion.

15. The incontinence article of claim 13, wherein a respective second joining region with an overall width P is arranged along said longitudinal periphery of said crotch portion in such a way that a ratio of the width P' to the width P''' is preferably between 1:4 and 4:1, between 1:3 and 3:1, between 1:2 and 2:1 or 1:1, wherein P' is a width of said subregion extended over by said second joining region.

16. The incontinence article of claim 13, wherein said second joining region is disposed parallel to said longitudinal direction and has a constant overall width.

17. The incontinence article of claim 13, wherein joining means in said second joining region are arranged in a point pattern and a sum of a surface area attached by said joining means assumes a proportion of at least 1.5%, at least 2.0%, at least 2.3%, at least 2.5%, at most 20.0%, at most 15.0%, at most 10.0%, at most 8.0%, at most 7.0% or at most 6.0%, with respect to an overall surface area extended over by said second joining region.

18. The incontinence article of claim 13, wherein said overhang of said backsheet material and/or of said topsheet material in said transverse direction summed over both sides of said longitudinal peripheries of said absorbent body, is at least 25%, 25-50%, 30-45% and or 35-45% of a greatest width (E) of said crotch portion.

19. An incontinence article in pants form for receiving body excretions, the article comprising:
    a front stomach portion;
    a rear back portion;

a crotch portion comprising an absorbent body, said crotch portion having an inner side an outer side as well as longitudinal peripheries and longitudinal ends, said crotch portion thereby extending in a longitudinal direction between said stomach portion and said back portion, wherein each of said stomach portion and said back portion has an inner side and a crotch-facing transverse periphery, said crotch portion thereby overlapping with said stomach portion in a front overlapping region and with said back portion in a rear overlapping region, said crotch portion further comprising a liquid-impermeable backsheet material and a topsheet material between which said absorbent body is disposed, said absorbent body also having longitudinal peripheries, at least one of said topsheet material and said backsheet material forming an overhang extending beyond said longitudinal periphery of said absorbent body;

two side seams generated by connecting together said stomach portion and said back portion by a manufacturer of the article on both sides thereof, said front stomach portion and said rear back portion thereby forming a stomach and back band which is continuous in a transverse or waist-encircling direction and defining a waist opening that is closed in said waist-encircling direction, wherein said crotch portion, said stomach portion and said back portion thereby also define leg openings of the incontinence article;

first elasticating means disposed in said stomach portion and said back portion, spaced apart from one another and extending parallel to one another in said transverse or waist-encircling direction to thereby elasticize said stomach portion and said back portion over surface areas thereof;

second elasticating means disposed in a crotch-side region of said stomach portion and of said back portion facing said leg openings;

a front connecting region disposed, structured and dimensioned to inseparably loin said outer side of said crotch portion to said inner side of said stomach portion; and a rear connecting region disposed, structured and dimensioned to inseparable join said outer side of said crotch portion to said inner side of said back portion, wherein said front and rear connecting regions of said stomach portion and of said back portion each respectively comprise a first joining region and second joining regions, said respective first joining region extending, at least in certain portions, beneath said absorbent body, wherein said second joining regions are disposed to bridge a respective said longitudinal periphery of said crotch portion and to extend over both a subregion of said overhang of said crotch portion and a subregion adjacent thereto of said stomach portion and/or of said back portion, a respective said second joining region extending in said longitudinal direction from a respective said crotch-facing transverse periphery of said stomach portion and/or said back portion towards said longitudinal ends of said crotch portion, said second joining regions being formed by joining means structured as welding locations, ultrasonic welding locations, thermal welding locations and/or calender welding locations, thereby forming reinforcing regions, wherein a ratio P'/N of a subregion of a respective said overhang that is extended over by said second joining region with a width (P'), to a respective side region of said stomach portion and/or of said back portion with a width (N), is at least 0.01, at least 0.015, at least 0.020, at most 0.35, at most 0.30, at most 0.25, at most 0.20, at most 0.15 or at most 0.10.

20. The incontinence article of claim 19, wherein said second joining regions and said reinforcing regions extend, as viewed in said longitudinal direction, from said crotch-facing transverse periphery of said stomach portion and of said back portion to at least a respective said longitudinal end of said crotch portion.

21. The incontinence article of claim 19, wherein a respective second joining region with an overall width P is arranged along said longitudinal periphery of said crotch portion in such a way that a ratio of the width P' to the width P''' is preferably between 1:4 and 4:1, between 1:3 and 3:1, between 1:2 and 2:1 or 1:1, wherein P' is a width of said subregion extended over by said second joining region.

22. The incontinence article of claim 19, wherein said second joining region is disposed parallel to said longitudinal direction and has a constant overall width.

23. The incontinence article of claim 19, wherein joining means in said second joining region are arranged in a point pattern and a sum of a surface area attached by said joining means assumes a proportion of at least 1.5%, at least 2.0%, at least 2.3%, at least 2.5%, at most 20.0%, at most 15.0%, at most 10.0%, at most 8.0%, at most 7.0% or at most 6.0%, with respect to an overall surface area extended over by said second joining region.

24. The incontinence article of claim 19, wherein said overhang of said backsheet material and/or of said topsheet material in said transverse direction summed over both sides of said longitudinal peripheries of said absorbent body, is at least 25%, 25-50%, 30-45% and or 35-45% of a greatest width (E) of said crotch portion.

* * * * *